United States Patent [19]

Macaluso, Sr. et al.

[11] 4,060,557
[45] Nov. 29, 1977

[54] HYDROFORMYLATION

[75] Inventors: Anthony Macaluso, Sr., Port Arthur; Lawrence F. Kuntschik, Nederland, both of Tex.

[73] Assignee: Texaco Inc., New York, N.Y.

[21] Appl. No.: 588,534

[22] Filed: June 19, 1975

Related U.S. Application Data

[63] Continuation-in-part of Ser. No. 366,387, June 4, 1973, abandoned.

[51] Int. Cl.$^2$ .............................................. C07C 45/08
[52] U.S. Cl. ...................... 260/604 HF; 260/632 HF
[58] Field of Search ...... 260/604 HF, 617 R, 632 HF

[56] References Cited

U.S. PATENT DOCUMENTS

| | | | |
|---|---|---|---|
| 2,609,337 | 9/1952 | Taylor | 260/604 HF |
| 2,696,506 | 12/1954 | Smith | 260/604 HF |
| 3,448,157 | 6/1969 | Slaugh | 260/604 HF |
| 3,620,283 | 11/1971 | Brown | 159/13 A |

*Primary Examiner*—James O. Thomas, Jr.
*Assistant Examiner*—W. B. Lone
*Attorney, Agent, or Firm*—Thomas H. Whaley; Carl G. Ries; Henry W. Archer

[57] ABSTRACT

Disclosed is a process for separating unreacted olefins, paraffins, aldehydes and alcohols from the catalyst and heavy ends from the hydroformylation process by using thin film distillation. In this process, the crude oxo product is metered into a thin film evaporator wherein the distillate containing olefins, paraffins, aldehydes and alcohols is rapidly separated by a continuous wiping action from the residue which contains the catalyst complex and the heavy ends. The various products are fractionated while the residue is directly recycled.

7 Claims, No Drawings

HYDROFORMYLATION

CROSS-REFERENCE TO CO-PENDING APPLICATION

This application is a continuation-in-part of coassigned U.S. application Ser. No. 366,387 filed June 4, 1973, and now abandoned.

BACKGROUND OF THE INVENTION

This invention is concerned with a method of processing the hydroformylation reaction product and catalyst to improve the overall economics and yield of the reaction.

This reaction and several modifications thereof are well-known in the art for producing aldehydes and/or primary "oxo" alcohols from olefins. The oxo alcohols find utility as solvents, lubricants, herbicides, odorants, and as intermediates in the manufacture of various plastics.

In the general case, the subject reaction involves the steps of contacting an olefinic hydrocarbon in the liquid phase with carbon monoxide and hydrogen at a temperature in the range of about 100° to 300° C. under a pressure of 1 to 2000 psig in the presence of a catalyst consisting of cobalt in complex combination with carbon monoxide and a trialkylphosphine ligand. The ratio of catalyst to olefin can be from about 1:1000 to about 10:1. The ratio of hydrogen to carbon monoxide can be from about 1:1 to about 10:1. The reactants include any aliphatic or cycloaliphatic compounds having at least one ethylenic carbon bond and nonhydrocarbons having such bonds. However, the main use of the reaction is the hydroformylation of olefins to form aldehydes and alcohols having one more carbon atom than the olefinic compound. The reaction can be illustrated by the following equation:

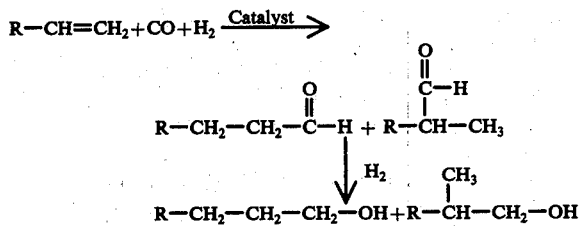

STATEMENT OF THE PRIOR ART

The prior art to which this invention relates, is aware, inter alia, of U.S. Pat. Nos. 2,779,802; 2,609,337; 2,683,752, 2,696,506; and of British Pat. No. 1,071,399. The first of these describes an improvement in the oxo process wherein an inert vapor is passed through the intermediate aldehydic product containing dissolved cobalt catalyst to facilitate its separation from the carbinol product. In U.S. Pat. No. 2,609,337 is described a flash distillation process for the treatment of a reaction product containing an aldehyde and a cobalt catalyst. Said process allows for extensive build up of catalyst residue on the heated surface; prolonged exposure of the catalyst residue to elevated temperature and increased catalyst decomposition. The process is concerned with aldehyde recovery but does not achieve reduced catalyst decomposition or catalyst recycle. In U.S. Pat. No. 2,683,752 the inventors disclose a method for extracting phenols from waste aqueous solutions by treatment with at least a fraction of the formylation bottoms of an oxo process. U.S. Pat. No. 2,696,506 shows an improved oxo process wherein the product is heated to decompose cobalt carbonyl into carbon monoxide and cobalt which deposits on a heated drum. In British Pat. No. 1,071,399, the oxo process is allowed to occur with the cobalt carbonyl catalyst solution being added to the hydroformylation reactor as a thin film.

SUMMARY OF THE INVENTION

In this process, the crude oxo product is metered to a thin film evaporator wherein the distillate, containing olefins, paraffins, aldehydes and alcohols, is separated from the residue containing catalyst complex and heavy ends by contacting with a heated surface for a very short residence time of 5 to 55 seconds. The distillate is collected and further vacuum fractionated to remove unreacted olefins and mixed paraffins from product aldehydes and alcohols. The aldehydes and alcohols fraction can then be hydrogenated and sent to an alcohol purification section. The entire residue containing the catalyst can be recycled directly to the oxo reactor, or mixed with fresh catalyst while being recycled to the oxo reactor; or a major portion of the residue (about 90%) can be recycled to the oxo reactor while the remaining residue portion proceeds to the catalyst recovery zone wherein fresh makeup catalyst is prepared and routed to the oxo reactor.

The present process centers around the use of a wiped film evaporator which separates aldehydes, alcohols, olefins and paraffins from the catalyst bottoms. The evaporator has rotating wiper blades which produce mechanically a thin film and continuously wipe this film on a heated surface. This mechanical wiping action provides a more rapid removal of the catalyst residue or bottoms and eliminates dependence on gravity flow. The process thus allows for: minimal build up of catalyst residue, due to the continuous wiping action; reduced catalyst decomposition and rapid continuous processing.

In the practice of the present process, the crude oxo product is charged to a thin film evaporator. A 2 inch diameter Turbo-Film Processor having 0.35 sq. foot evaporative surface was used at a rate ranging from 25 to 150 cc/hour (preferably 60 cc/hour). Distillation temperatures from 150° to 500° F. (preferably from 200° to 250° F.) and pressures from 0.001 to 50 mm Hg (preferably from 0.001 to 10 mm) can be employed. The catalyst complex can be any metal metal carbonyls or metal complexes capable of catalyzing the oxo reaction (preferably dicobalt octacarbonyl in complex combination with tri-n-butylphosphine). The cobalt source can be dicobalt octacarbonyl, the cobalt salt of an organic salt (preferably cobalt stearate), or cobalt itself. The ligand can be any organophosphine (preferably tri-n-butylphosphine), - phosphite, - phosphate or phosphonate or other ligands used for complexing oxo catalysts.

The completeness of separation of the crude reaction product from the catalyst-heavy ends is dependent on the thin film distillation temperature, pressure and rate. Thus a rate sufficient to effect substantially complete separation at the operating temperature and pressure should be used.

The process is adaptable to a wide range of olefins by proper selection of thin film evaporation conditions. Thus $C_2$–$C_{30}$ alpha, internal and mixed olefins can be treated by the present process. These olefins include those derived by dehydrogenation of paraffins, wax cracking, olefin polymerization and the like.

In a commercial process the crude oxo product is distilled under vacuum to remove unreacted olefins and paraffins. The bottoms are then further distilled under vacuum to separate the aldehydes and alcohols from the catalyst complex and the heavy ends. The aldehydes and alcohols fraction are then sent to the hydrogenation section; while about 90% of the heavy ends and catalyst bottoms are recycled directly to the oxo reactor. Thus in this commercial process the catalyst complex is subjected to two high temperature vacuum distillations. This lengthy contact time at relatively high temperatures augments the possibility of some catalyst complex decomposition which results in decreased catalyst life and increased costs. In the present process, the catalyst complex experiences a once-through distillation for a relatively short contact time at lower temperatures and thereby reduces catalyst decomposition. This reduction in catalyst decomposition affords the inherent advantage of extended catalyst life. As shown in the illustrative examples below, the catalyst recovered by this process also results in improved selectivity to alcohols with extended use of the recycled catalyst.

A comparison of distillation time, and bottoms temperature vs. catalyst decomposition is given below:

|  | Thin Film | Commercial Process | Conventional Vacuum Dist. |
|---|---|---|---|
| Distillation Technique Catalyst Complex Exposure Time to Heated Surface | <1 minute | About 2 hours | 5–10 hrs |
| Bottom Temperature, °F | 200–250 | About 1 hr at 370° F About 1 hr at 428° F | 200–450 |
| Condition of Catalyst after Distillation | Very little decomposition Catalyst could be recycled | Some catalyst decomposition Necessary to regenerate part of catalyst | Essentially complete catalyst decomposition |

The invention is illustrated by the following examples:

EXAMPLE I

Cobalt stearate (51.4 g., 0.06 mols of cobalt), tri-n-butylphosphine (12.6 g., 0.06 mols) and the $C_{11}$–$C_{14}$ alpha olefins from wax cracking (345.6 g., 2.0 mols) were added to a 1000 ml stainless steel autoclave and the reactor was flushed with synthesis gas (hydrogen:carbon monoxide molar ratio of 2), pressured to 700 psig and heated to reaction temperature (340° F). Once the reaction temperature was reached, the reactor was pressured with the synthesis gas (hydrogen:carbon monoxide molar ratio of 2) to 1300 psig. The reaction was allowed to continue until no further uptake of the synthesis gas was observed. At the end of this time (90 minutes), the autoclave was cooled, vented and emptied. The crude reaction mixture was then thin film distilled at 200° F., maximum vacuum and an average charge rate of 60 ml/hour to separate unreacted olefins, mixed paraffins, aldehydes and/or alcohols from the catalyst complex and heavy ends. The overhead distillate was then vacuum fractionated to remove unreacted olefins and mixed paraffins. Next the product alcohols were taken overhead in 57 mol % selectivity while olefin conversion was calculated as 93 wt. %. Ninety weight percent of the catalyst complex and heavy ends was recycled as catalyst for the next reaction (Example 2).

EXAMPLE II

The $C_{11}$–$C_{14}$ alpha olefins from wax-cracking (345.6., 2.0 mols) and the catalyst complex and heavy ends from Example I (84.2 g., 90% of thin film distillation residue recovered from Example I) were added to a 1000 ml stainless steel autoclave and the reactor was flushed with synthesis gas (hydrogen:carbon monoxide molar ratio of 2), pressured to 700 psig and heated to reaction temperature (340° F). Once reaction temperature was reached, the reactor was pressured with the synthesis gas (hydrogen: carbon monoxide in a molar ratio of 2) to 1300 psig. The reaction was allowed to continue until no further up-take of the synthesis gas was observed. At the end of this time (90 minutes), the autoclave was cooled, vented and emptied. The crude reaction mixture was then thin film distilled at 200° F. under maximum vacuum and at an average charge rate of 60 ml/hour to separate unreacted olefins, mixed paraffins, aldehydes and/or alcohols from the catalyst complex and heavy ends. The overhead distillate was then vacuum fractionated to remove the unreacted olefins and the mixed paraffins. The product alcohols were then taken overhead in 73 mol % selectivity. Olefin conversion was calculated as 99 wt. %. Ninety weight percent of the catalyst complex and heavy ends was recycled as catalyst along with fresh makeup catalyst for the next reaction (Example III).

EXAMPLE III

The $C_{11}$–$C_{14}$ alpha olefins from wax cracking (345.6., 2.0 mols), catalyst and heavy ends from Example II (72.0g., 90% of thin film distillation residue recovered from Example II), and cobalt stearate and tri-n-butylphosphine (5.0 g., and 2.5 g., respectively, added as fresh "make-up" catalyst) were added to a 1000 ml stainless steel autoclave and the reactor was flushed with synthesis gas (hydrogen: carbon monoxide molar ratio of 2), pressured to 700 psig and heated to reaction temperature (340° F). Once reaction temperature was reached, the reactor was pressured with the synthesis gas (hydrogen:carbon monoxide in a molar ratio of 2) to 1300 psig. The reaction was allowed to continue until no further uptake of the synthesis gas was observed. At the end of this time (90 minutes), the autoclave was cooled, vented and emptied. The crude reaction mixture was then thin film distilled at 200° F., maximum vacuum and an average charge rate of 60 ml/hr to separate unreacted olefins, mixed paraffins, aldehydes and/or alcohols from the catalyst complex and heavy ends. The product alcohols were taken overhead in 87 mol. % selectivity. Olefin conversion was calculated as 94 wt. %

Since catalyst decomposition is held to a minimum by use of the thin film separation, the present invention allows for direct recycle of the catalyst bottoms to the oxo reactor. Direct recycle of the catalyst bottoms eliminates costly catalyst recovery and the regeneration step generally required when conventional vacuum distillation conditions are employed.

What is claimed is:

1. In a process for the production of aldehydes and alcohols by contacting olefins of the group of $C_{11}$–$C_{14}$ alpha olefins with carbon monoxide and hydrogen in a hydroformylation zone at a temperature of about 100° to about 300° C. under a pressure of 1 to 200 psig in the presence of a cobalt catalyst consisting of cobalt in complex combination with carbon monoxide and a tertiary organo-phosphine to form a product phase containing unreacted olefins, paraffins, saturated aldehydes and alcohols, catalyst residue and heavy end; which are separated, the improvement whereby said separation is effected by the steps of metering said phase to a thin film evaporating zone, mechanically forming a thin film of said phase on a heated surface; continuously wiping said film on said surface at a temperature range of 200° to 250° C for an exposure time for said residue of 5 to 55 seconds thereby separating a distillate containing unreacted olefins, paraffins, aldehydes and alcohols, from said catalyst residue and heavy end; fractionating said distillate to separate the components thereof and directly recycling at least a part of said residue to said hydroformylation zone.

2. The process of claim 1 wherein said distillation is carried out at a temperature of 150° to 500° F. under a pressure ranging from 0.001 to 50 mm Hg.

3. The process of claim 1 wherein said distillation is carried out at a temperature ranging from 150° to 250° F. under a pressure ranging from 0.001 to 10 mm Hg.

4. The process of claim 1 wherein said olefins consist of $C_{11}$–$C_{14}$ alpha olefins obtained by wax cracking.

5. The process of claim 1 wherein the entire residue is recycled to the hydroformylation zone.

6. The process of claim 7 wherein said residue is mixed with fresh make up catalyst as it is recycled to said zone.

7. The process of claim 1 wherein the major portion of said residue is recycled to said hydroformylation zone while the remainder is passed to a catalyst recovery zone and then sent to said hydroformylation zone.

* * * * *